(12) United States Patent
Hamby et al.

(10) Patent No.: US 7,715,008 B2
(45) Date of Patent: May 11, 2010

(54) SYSTEM AND METHOD OF OPTICALLY MONITORING CONTAMINATION OF A MACHINE COMPONENT

(75) Inventors: Eric Scott Hamby, Fairport, NY (US); Frank John Bonsignore, Rochester, NY (US); Phillip Stephen Crispino, Webster, NY (US); R. Enrique Viturro, Rochester, NY (US)

(73) Assignee: Xerox Corporation, Norwalk, CT (US)

( * ) Notice: Subject to any disclaimer, the term of this patent is extended or adjusted under 35 U.S.C. 154(b) by 250 days.

(21) Appl. No.: 12/053,075

(22) Filed: Mar. 21, 2008

(65) Prior Publication Data

US 2009/0237645 A1 Sep. 24, 2009

(51) Int. Cl.
*G01N 21/25* (2006.01)
(52) U.S. Cl. ..................................................... 356/417
(58) Field of Classification Search .................. 356/417
See application file for complete search history.

(56) References Cited

U.S. PATENT DOCUMENTS

| | | | |
|---|---|---|---|
| 5,554,480 | A | 9/1996 | Patel et al. |
| 6,002,893 | A | 12/1999 | Caruthers, Jr. et al. |
| 7,038,833 | B1 | 5/2006 | Liu et al. |
| 7,193,696 | B2 * | 3/2007 | Engelbart et al. ......... 356/237.1 |
| 7,257,337 | B2 | 8/2007 | Amico |
| 7,339,657 | B2 * | 3/2008 | Coates ......................... 356/73 |
| 2004/0201835 | A1 * | 10/2004 | Coates et al. .................. 356/73 |
| 2005/0225753 | A1 * | 10/2005 | Engelbart et al. ......... 356/237.1 |
| 2008/0231851 | A1 | 9/2008 | Pan et al. |
| 2008/0232826 | A1 | 9/2008 | Pan et al. |

OTHER PUBLICATIONS

U.S. Appl. No. 11/904,267, filed Sep. 26, 2007, Moore et al.

* cited by examiner

*Primary Examiner*—Roy Punnoose
(74) *Attorney, Agent, or Firm*—Carter, DeLuca Farrell & Schmidt, LLP (57) ABSTRACT

A system and method for optically monitoring contamination of machinery includes an optical illumination source, a photodetector and an analysis module. The system and method can monitor a fuser roll, a fuser belt, or other printer module component. The optical illumination source can emit at least one illuminating frequency. The at least one illuminating frequency is configured to cause a contaminant marker to fluoresce at least one fluorescing frequency and is also configured to at least partially illuminate the machine component. The machine component contains the contaminant marker when at least partially contaminated. The photodetector is responsive to the at least one fluorescing frequency and detects the at least one fluorescing frequency emitted from the contaminated machine component. The analysis module is in operative communication with the photodetector and is figured to receive a signal therefrom. The analysis module is configured to estimate contamination of the machine component as a function of the signal from the photodetector.

25 Claims, 8 Drawing Sheets

SYSTEM AND METHOD OF OPTICALLY MONITORING CONTAMINATION OF A MACHINE COMPONENT

BACKGROUND

1. Technical Field

The present disclosure relates to monitoring a machine component, and in particular, to a system and method for optically monitoring contamination of a machine component, such as a printer machine component, utilizing fluorescent contaminant markers.

2. Description of Related Art

Modern machine designs utilize various "machine components" that are used together to fully construct the machine. These machine components may be replaceable and/or permanent. For example, modern printing systems utilize various modular and integrated machine components. Machine components utilized in printing systems are referred to herein as printer machine components. Monitoring of these printer machine components may be implemented using one or more strategically placed sensors. Some of these sensor may be optically based sensors. One such optical monitoring technique is described in the previously filed U.S. Patent Application entitled, "SYSTEM AND METHOD FOR MONITORING A PRINTING SYSTEM USING A CAMERA", filed on Sep. 26, 2007 and assigned U.S. patent application Ser. No. 11/904,267, which has been assigned to the present assignee, and the entire contents thereof, are hereby incorporated by reference.

Many printer machine components are replaceable and have a limited shelf life and/or useful life. For example, in some color printing systems four types of toners are deposited on a printing substrate (e.g., paper) from one or more drums to form a toner image; however, the toner image initially deposited onto the paper is not fully secured to the paper. Moreover, the toner image initially deposited onto the paper does not have the desired gloss level. The toner image is permanently fixed to the paper and the desired gloss level in the image are both achieved by using a heat and pressure mechanism or a radiant fusing technology to melt and bond the toner particles to the medium being printed on (usually paper). This process is called fusing. These fusing members have a limited useful life.

One type of fusing member is a fuser roll. Typically, a pair of cylindrically shaped machine components forms the fuser rolls (one applies heat and the other applies pressure). The fuser rolls are used to fuse the toners to the paper. The toner image on the substrate initially has the consistency of loose powder. The substrate (e.g., paper) with the loose toner image is fed through the two fusing members where the toner image is heated while sufficient pressure is applied. The pressure and heat applied should be properly controlled to ensure that the toner image is adequately bonded to the substrate and to achieve the desired level of image gloss.

Another type of fusing member is a fuser belt. Rather than use a pair of fuser rolls, one or more belts are used to move the substrate along a path. The belt may be wrapped and/or guided along a path with various rollers and/or nips. One or more belts can carry the substrate with a loose toner image disposed thereon through a region of the printing system so that heat and/or pressure is applied to fuse the toner to the substrate.

The fuser belt and fuser roll are only two types of fusing members that can be utilized in the fusing process. Other fusing members include the various gears, nips, rollers and components used in the fusing process as well. One possible failure mode of fusing members is toner contamination. For example, fuser rolls eventually accumulate toner contamination levels that cause visible defects on the end product (e.g., a printed piece of paper). Fusing member contamination can cause various visible print quality defects associated with the toner offsetting onto the fuser member. Because of this type of failure mode, the fusing member(s) must be periodically replaced. This type of failure mode can account for a significant portion of the overall replacement costs of all of the printer machine components. One technology that extends the useful life of a fusing member is to continuously apply oil to the fusing member to prevent the toner from sticking thereto; although the useful life of the fusing member is extended, eventually it must be replaced.

One method of estimating contamination of the fusing member is destructive and off-line. This approach requires the removal of a strip of rubber from the fuser roll (or belt) with examination of the strip using Fourier transform infrared spectroscopy analysis of the sample to quantify the amount of various contaminants on the fuser roll (or belt). This method permanently disables the fusing member, is very expensive, and is not well suited for in situ diagnostics and/or feedback control.

SUMMARY

The present disclosure relates to monitoring a machine component, and in particular, to a system and method for optically monitoring contamination of a machine component, such as a printer machine component, utilizing fluorescent contaminant markers. The system and/or method may be at least partially implemented by an operative set of processor executable instructions configured for execution by at least one processor.

In one embodiment of the present disclosure, the system for optically monitoring contamination of machinery includes an optical illumination source, a photodetector and an analysis module. The monitored machine component may be a printer machine component, a fusing member, a fuse roll, a fuser belt or the like. The optical illumination source emits at least one illuminating frequency that is configured to cause a contaminant marker to fluoresce at least one fluorescing frequency. The optical illumination source at least partially illuminates the machine component. The machine component contains the contaminant marker when at least partially contaminated. The contaminant may be cyan toner, magenta toner, yellow toner, black toner or other debris. The contaminant marker may be rhodamine dye as already included in some formulations of the magenta toner and/or other contaminant markers. The optical illumination source may be a near-ultraviolet source and/or may be a black light.

The photodetector is responsive to at least one fluorescing frequency and is configured to detect the at least one fluorescing frequency emitting from a contaminated machine component. The analysis module is in operative communication with the photodetector and receives a signal therefrom. The analysis module estimates contamination of the machine component as a function of the signal from the photodetector. The photodetector may be part of a full-width array sensor or a camera, e.g., a CCD or CMOS camera.

In another embodiment of the present disclosure, the system may include an alert module, an indicator module and/or a sensor controller. The alert module is in operative communication with the analysis module and can issue an alert when the estimated contamination of the machine component exceeds a threshold. The indicator module is in operative communication with the analysis module and can provide one or more indications corresponding to the estimated contamination of the machine component. For example, the indicator module may provide a "gas gauge" type display to visually indicate to a person how much useful life of a fusing member remains. The sensor controller is in operative communication with the analysis module and the photodetector. The sensor controller can calibrate the analysis module by estimating one or more background levels (discussed in more detail below).

In yet another embodiment of the present disclosure, the system may further include a control module and/or a coordinating module. The control module is in operative communication with the analysis module and provides a control signal. The control signal is a function of the estimated contamination of the machine component. For example, when the machine component is a fusing member the control signal may be configured to control at least one fusing parameter such as fusing temperature, an oil rate, a fusing pressure, a registration, and/or a registration offset. Additionally or alternatively, when the machine component is a printer machine component, the coordinating module can adjust a job schedule, a sheet schedule, a fuser schedule and/or a print engine schedule to account for the estimated contamination.

In another embodiment of the present disclosure, the estimated contamination of the machine component is a function of at least one of a spatial value and a temporal value. For example, the estimated contamination of the machine component may be utilized to generate a contamination spatial map that is periodically updated in time as new contamination measurements become available.

In yet another embodiment of the present disclosure, the system may include a multi-channel optical sensor that includes the photodetector (e.g., an RGB sensor), and the analysis module may be in operative communication with the multi-channel optical sensor and receives the signal from the multi-channel optical sensor. The analysis module may estimate contamination of the machine component using a parameterized model and/or one or more of first, second, third, fourth, and fifth functions. The parameterized model relates the contamination of the machine component to the signal from the multi-channel optical sensor. The first function relates the contamination of the machine component to an area between a channel signal of the signal from the multi-channel optical sensor and a background level of the channel signal of the signal from the multi-channel optical sensor. The second function relates the contamination of the machine component to a maximum difference between the channel signal of the signal from the multi-channel optical sensor and the background level of the channel signal of the signal from the multi-channel optical sensor. The third function relates the contamination of the machine component to an area under the channel signal of the signal from the multi-channel optical sensor. The fourth function relates the contamination of the machine component to a peak value of the channel signal of the signal from the multi-channel optical sensor. The fifth function relates the contamination of the machine contamination of the machine component utilizing the background level of the channel signal of the signal from the multi-channel optical sensor.

In yet another embodiment of the present disclosure, a method for optically monitoring contamination of machinery includes the steps of providing an optical illumination source and an analysis module, and estimating the contamination of the machine component. The machine component may be a printer machine component such as a fusing member. Two types of fusing members are a fuser roll and a fuser belt. The method may further include the step of adding the fluorescent marker to a contaminant.

In another embodiment of the present disclosure, the method may include the steps of replacing the machine component when the estimated contamination of the machine component exceeds a threshold and/or issuing an alert when the estimated contamination of the machine component exceeds a threshold. The method may provide a control signal that controls one or more fusing parameters, such as a fusing temperature, an oil rate, a fusing pressure, a registration and/or a registration offset. The method may also adjust one or more of a job schedule, a sheet schedule, a fuser schedule and/or a print engine schedule to account for the estimated contamination.

BRIEF DESCRIPTION OF THE DRAWINGS

These and other advantages will become more apparent from the following detailed description of the various embodiments of the present disclosure with reference to the drawings wherein.

DETAILED DESCRIPTION

Figure 1:
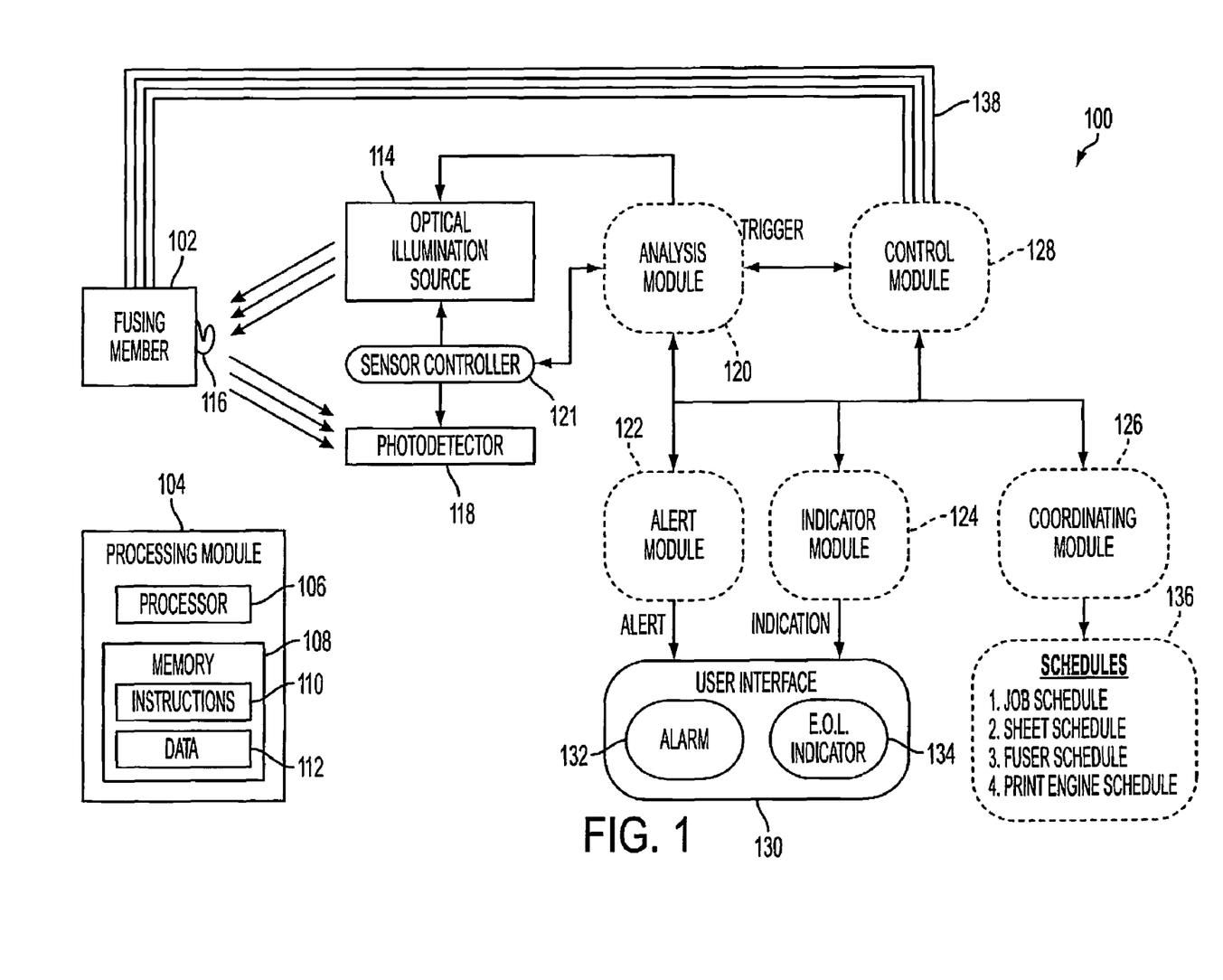
FIG. 1 is a block diagram of a system that can optically monitor contamination of a printer machine component utilizing fluorescent contaminant markers in accordance with the present disclosure.

Referring to the drawings, FIG. 1 is a block diagram of a system 100 that can optically monitor contamination of a printer machine component, e.g. fusing member 102, utilizing fluorescent contaminant markers in accordance with the present disclosure.

System 100 can monitor contamination of a machine component such as a printer machine component and is shown in FIG. 1 as being configured to monitor fusing member 102. System 100 may be implemented and/or controlled by processing module 104 having processor 106 and memory 108. Memory 108 includes instructions 110 and data 112. Instructions 110 may implement and/or control a portion or all of system 100. System 100 may be implemented in hardware, software, software in execution, firmware, microcode, bytecode, the like or any combination thereof.

System 100 uses an optical illumination source 114 that can emit light of a single optical frequency, multiple optical frequencies, or a band of optical frequencies. Additionally or alternatively, optical illumination source 114 can emit visible and/or invisible optical light. For example, optical illumination source 114 may emit near-ultraviolet or ultraviolet light.

Illumination source 114 at least illuminates the fusing member 102 such that the optical frequency being emitted can cause a contaminant marker within contaminant 116 to florescence. Frequencies which cause the contaminate marker to fluoresce are referred to as illuminating frequencies. Fluorescence is a type of luminescence in which a molecule (e.g., the contaminant marker) absorbs a photon thus triggering the emission of another photon with a different frequency (or wavelength). A frequency emitted by the molecule is referred to as an fluorescing frequency. Contaminant 116 includes a contaminant marker, for example, contaminant 116 may be magenta toner and the contaminant marker may be rhodamine dye included within the magenta toner (discussed in more detail below). Additionally or alternatively, the fluorescent marker may be added to the contaminant (also discussed in more detail below). Other colors of a printer's color gamut (e.g., each of the CMYK toners) may be the contaminant. The contaminant may also be debris.

Optical illumination source 114 illuminates fusing member 116 to cause a contaminant marker of contamination (e.g., contaminant 116) to fluorescence so that photodetector 118 can detect the optical frequency at which the contaminant marker is fluorescing. Photodetector 118 may be any sensing member responsive to the optical frequency emitted by the contaminant marker. For example, photodetector 118 may be a sensing member as found a CCD camera, a CMOS camera, a full-width array sensor or the like. Additionally or alternatively, photodetector 118 may be part of a multi-channel optical sensor such as typically found in RGB cameras.

System 100 also includes analysis module 120. Analysis module 120 is in operative communication with sensor controller 122. Analysis module 120 receives a signal from sensor controller and can process the signal to estimate contamination of a machine component, e.g., fusing member 102. The signal received from sensor controller 122 may be in analog and/or digital form and may have one or more channel signals. For example, the signal received by analysis module 120 from sensor controller 122 may include three channel signals each corresponding to a "blue", "red" and "green" channel. The signal may also be image data and analysis module 120 may include image processing hardware, software, firmware and/or the like. Analysis module 120 can estimate contamination of fusing member 102 as a function of the signal from sensor controller 122 (discussed in more detail below) and communicate the estimated contamination to alert module 122, indicator module 124, coordinating module 126, and/or control module 128.

Analysis module 120 may also control and/or instruct sensor controller 122. For example, analysis module 120 may receive a trigger signal from control module 128 and may instruct sensor controller 122 to turn "on" optical illumination source 114 to cause a contaminant marker to fluoresce. Sensor controller 122 may then instruct photodetector 118 to "take a picture" (e.g., when photodetector is part of a RGB CCD camera) and relay the signal to analysis module 120.

As mentioned above, analysis module 120 is in operative communication with sensor controller 122 and sensor controller 122 is in operative communication with optical illumination source 114 and photodetector 118 and. Sensor controller 122 may directly calibrate photodetector 118, e.g., by adjusting a current bias, or may provide calibration information to analysis module 120. However, in a different embodiment not depicted in FIG. 1, sensor controller 122 may be part of analysis module 120. Sensor controller 122 can provide to analysis module 120 calibration data such as a background level of one channel signal included in the signal from sensor controller 122, e.g., the background level of a blue channel signal may be the amount of light that causes a blue photodetector of a RGB sensor to respond to an illuminated region of fusing member 102 that is highly unlikely to have any amount of contamination such as a far end of a fuser roll. Additionally or alternatively, the background level may be from ambient light, optical noise, electrical noise, thermal radiation or the like.

Alert module 122 can issue an alert when the estimated contamination of fusing member 102 reaches a threshold. The issued alert may be an alert signal, a digital data structure (e.g., a flag), an alarm, a visual indicator or the like. For example, the issued alert may be received by user interface 130 that activates alarm 132. Alarm 132 may be a visual alarm, a sound, a pop-up dialog box, or the like that can notify a user of the printing system having fusing member 102 that the fusing member needs maintenance, that the fusing member needs to be replaced (or replaced shortly) or the like.

Indicator module 124 provides an indication corresponding to the estimated contamination of the machine component, e.g., an indication signal, which may be received by user interface 130. Additionally or alternatively, indicator module 124 may provide an indication as to how much useful life remains with the fusing member (i.e., the end of life). The end of life calculation may be based on usage (e.g., pixel usage), the amount of estimated contaminant 116 as estimated by analysis module 120, pixel count, pages printed, time in machine and the like, or some combination thereof. For example, end of life indicator 134 in user interface 130 may be a "gas gauge" type display showing a user how much useful life is left of fusing member 102.

System 100 also includes coordinating module 126 that is in operative communication with analysis module 120. Coordinating module 126 can utilize the estimated contamination of fusing member 102 to adjust one of schedules 136. Schedules 136 may be a schedule as found on a printing system. Schedules 136 include a job schedule, a sheet schedule, a fuser schedule and a print engine schedule. For example, a certain portion of fusing member 102 may be contaminated beyond a threshold and coordinating module may re-prioritize jobs so that the contaminated portion is not utilized, thus extending the useful life of fusing member 102. Additionally or alternatively, if system 100 it utilized by a printing system with multiple fusing members and one fusing member has contamination beyond a threshold, substrates (e.g., paper) can be routed to avoid the contaminated fusing member; or if the machine component being monitored is a print engine component of a printing system with multiple print engines, the substrates may be routed to other print engines to avoid the print engine that is contaminated beyond the threshold.

System 100 also includes control module 128 that provides a control signal or signals that are communicated over a bus. Control module 128 may provide a control signal that accounts for the estimated contamination of fusing member 102 received from analysis module 120. For example, control module 128 can provide a control signal in a feedback loop where the estimated contamination of fusing member 102 is the error signal (e.g., such as in a PID algorithm). Control module 128 may control a fusing parameter of fusing member 102 such as a fusing temperature, an oil rate, a fusing pressure, a registration, a registration offset and/or the like.

Figure 2:
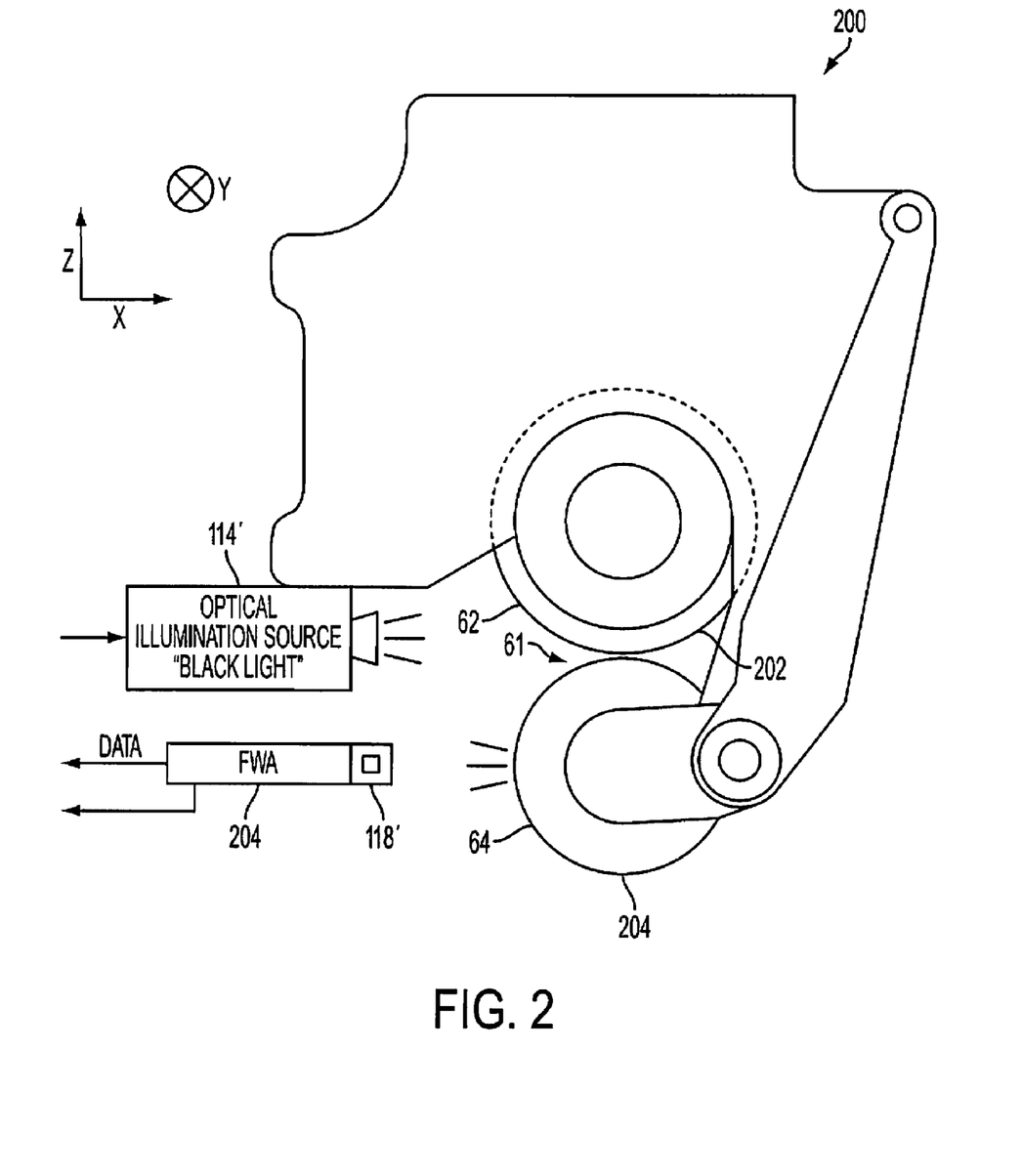
FIG. 2 is a side-view schematic of a fusing member including two fuser rolls with an optical illumination source and a full-width array sensor for monitoring contamination in accordance with the present disclosure.

Referring now to FIGS. 1 and 2, FIG. 2 is a side view of fusing system 200 that includes fusing rolls 202 and 204. Fusing system 200 may be part of a system for monitoring contamination of machinery such as system 100 of FIG. 1. Fusing roll 202 applies heat while fusing roll 204 applies pressure. Full width array sensor 204 is shown and includes photodetector 118'. Note the three-axes in FIG. 2 with the y-axis going into the page. Full width array 204 is positioned along the length of roll 204. Photodetector 118' may be photodetector 118 of FIG. 1. Optical illumination source 114' is shown and may be optical illumination source 114 of FIG. 1. Optical illumination source 114' can illuminate fusing rolls 202 and/or 204 across the entire length while full width array 204 can sense a fluorescing contaminant marker along the entire length as well. This may be utilized to provide localized contamination estimations and is discussed in more detail below.

Figure 3:
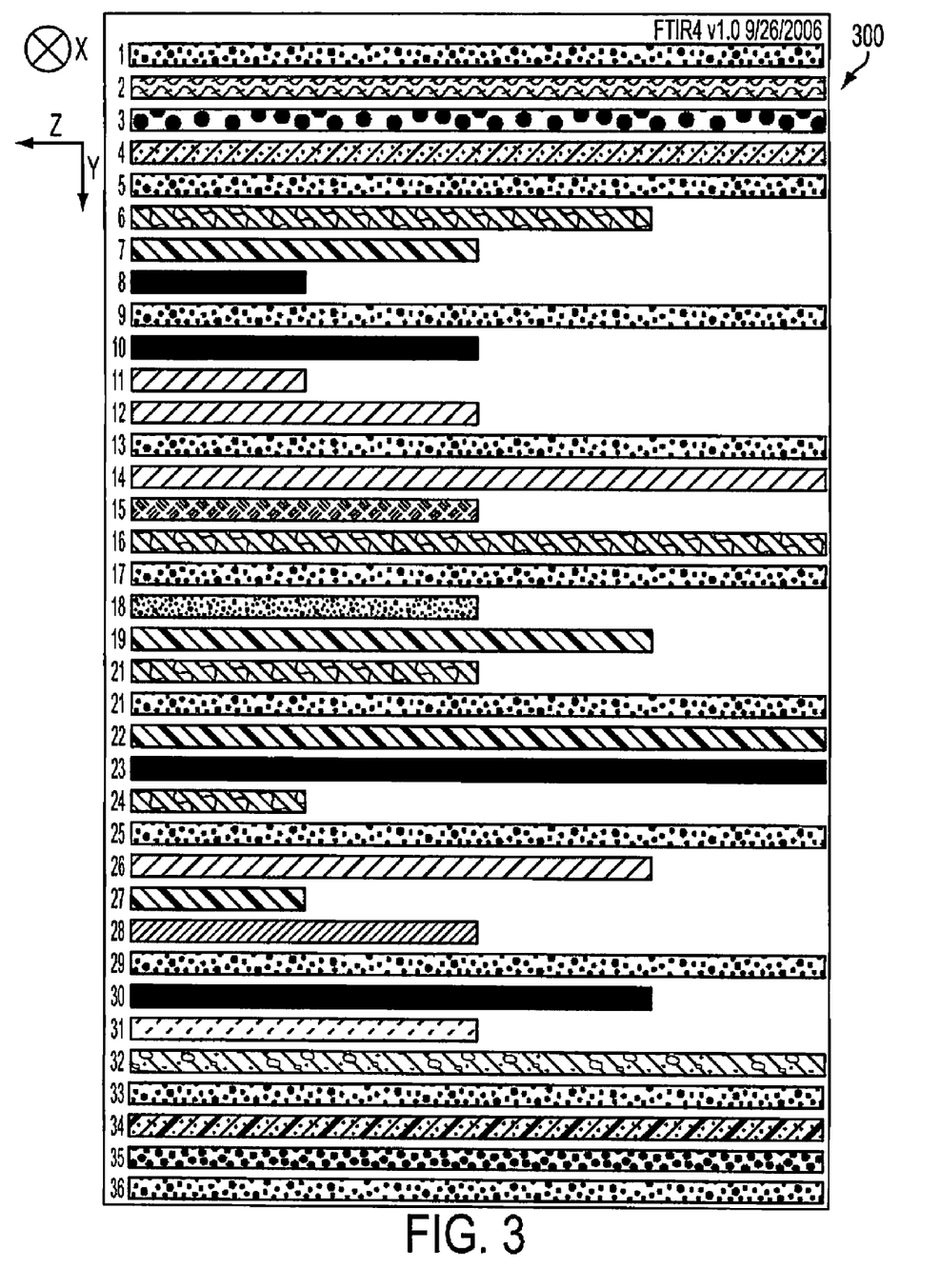
FIG. 3 is a graphic representation of a stripe test pattern that is utilized in accelerated useful life testing on fusing members in accordance with the present disclosure.

Referring now to FIG. 3, consider an exemplary accelerated life test that can be conducted by printing stripe test pattern 300 using fusing system 200. Note the axes in the upper right hand corner of FIG. 3. Test stripe pattern 300 can be repeatedly printed causing multiple substrates to be processed by a fusing member, such as fusing rolls 202 and 204. This test can reduce the amount of useful life of the fusing members and can be used to simulate wear and tear, and contamination that occurs over a long period of time in a relatively short period of time, hence the name "accelerated life testing". Test stripe pattern 300 includes stripes 1 through 36, each being a single color. Some stripes have a single colorant (e.g., cyan toner only) and others have a combination of colorants, however all stripes have a uniform color throughout. The length (i.e. the distance of the stripe along the z-axis) varies so that differing sections of a fusing member (e.g., fuser roll 204) may be exposed to identical stripe colors (of stripes 1 through 36) but different "accelerations" during accelerated life testing; for example, a stripe twice as long as another stripe but having the same color should cause contaminate buildup that is equivalent to double the use.

One previously used approach for accelerated fuser life testing utilized test stripe pattern 300 to print a sufficient number of copies (machine dependant) onto pieces of substrate using fusing members (e.g., fusing rolls 202 and 204) and measuring the contamination. The contamination was measured by destroying the fusing members by extracting strips of rubber and conducting a Fourier transform infrared spectroscopy analysis of the sample(s) to quantify the various amounts of contaminants on the fusing member. However, as previously mentioned, system 100 of FIG. 1 can monitor the contamination in situ and in real-time.

An example accelerated fuser life experiment that may be utilized to calibrate system 100 of FIG. 1 and/or compare system 100 of FIG. 1 to a reference involves printing test stripe pattern 300 multiple times to accelerate the time it takes to reach an end of life of a fuser roll, and repeating the process on a total of 6 fuser rolls. Additionally, the experiment may involve comparing the estimated contamination using an optical illumination source (e.g., optical illumination source 114') to off-line destructive testing. Each measurement can be repeated twice to create a total of 12 measurements.

Figure 4A:
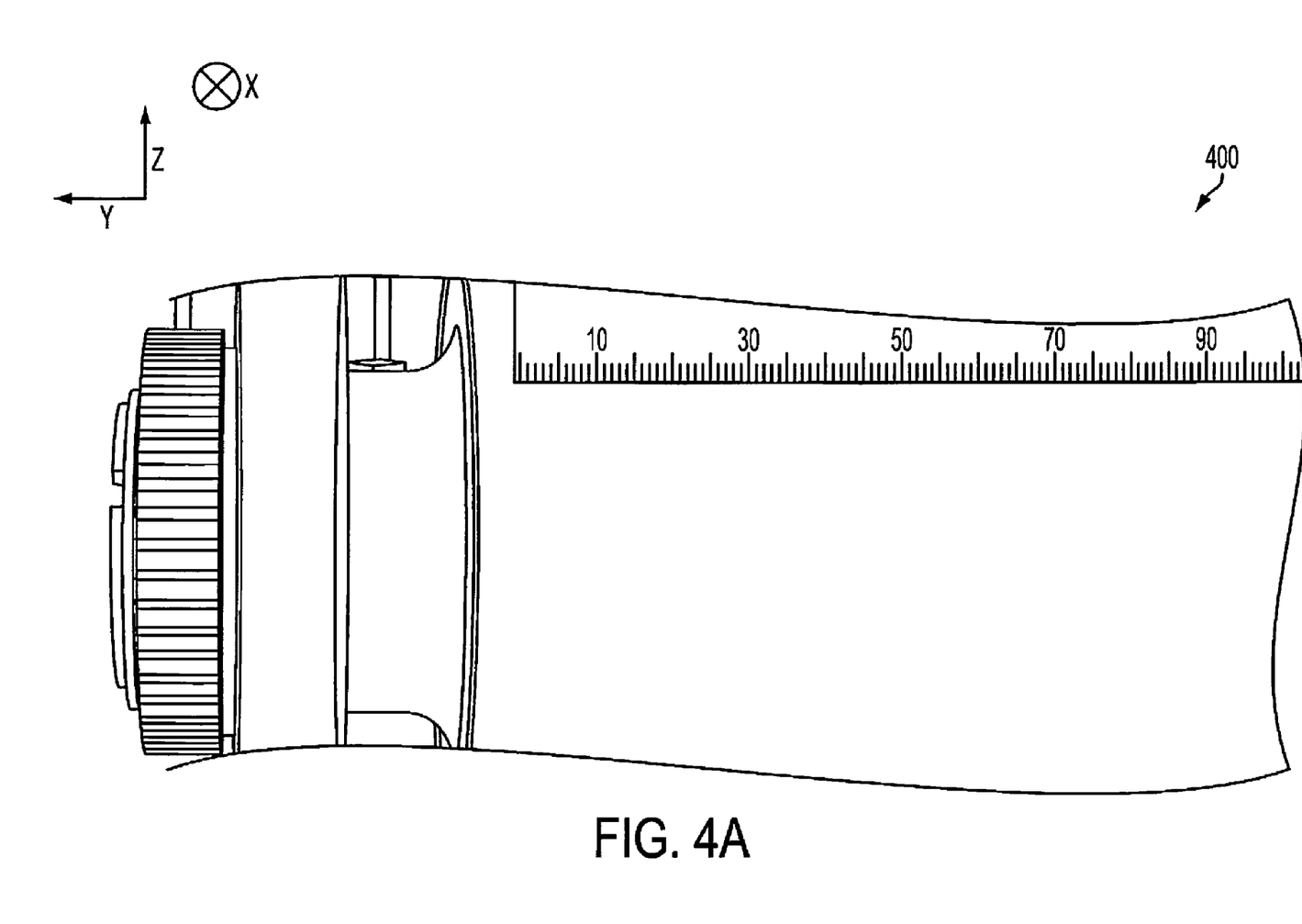
FIGS. 4A and 4B are graphic representations of two front-view photographs of a fuser roll containing a contaminant with FIG. 4B taken while the fuser roll is optically illuminated by an optical illumination source causing a contaminant marker to fluoresce in accordance with the present disclosure.
Figure 4B:
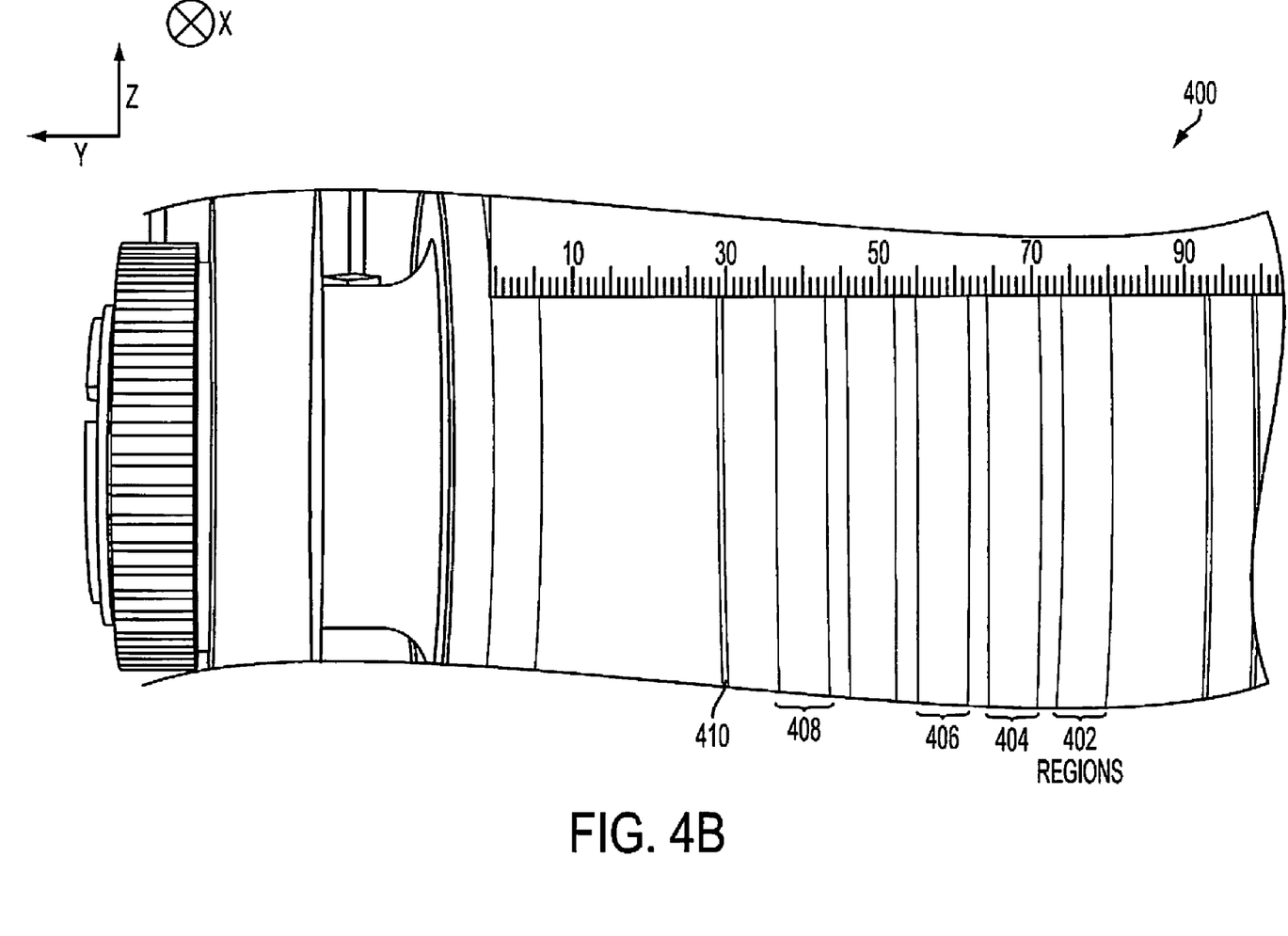

Referring now to FIGS. 3, 4A and 4B, FIGS. 4A and FIG. 4B are graphic representations of two front-view photographs of a fuser roll 400 containing a contaminant with FIG. 4B taken while being illuminated (e.g., by optical illumination source 114 of FIG. 1). Note that in FIG. 4B the optical illumination source is causing the contaminant marker to fluoresce on fuser roll 400 making regions 402 through 410 visible thus revealing the contamination. Each of regions 402 through 410 of the fuser roll 400 was exposed to a stripe with magenta color that deposited a contaminant marker therein which is fluorescing in FIG. 4B. The contaminant marker may be from a chemical reaction occurring on fuser roll 400 and/or may be the rhodamine dye as found in magenta toner. Because the stripes of FIG. 3 were repeatedly printed using fuser roll 400, the repeated printing had one or more toner colors that contaminated fuser roll 400. The differing intensities of regions 402 through 410 are a result of different "end of life" acceleration values as implemented by the differing lengths of each respective stripe of test stripe pattern 300 and/or the amount of magenta toner needed to print one of the respective stripes of test stripe pattern 300.

As previously mentioned, FIG. 4A shows fuser roll 400 when viewed under ambient light, and FIG. 4B shows fuser roll 400 when viewed under illumination, e.g., illumination by a black light. Because of the fluorescence occurring from the contaminant marker, the individual stripes corresponding to the stripes of test pattern 300 of FIG. 3 are readily apparent in FIG. 4B as compared to FIG. 4A.

Figure 5:
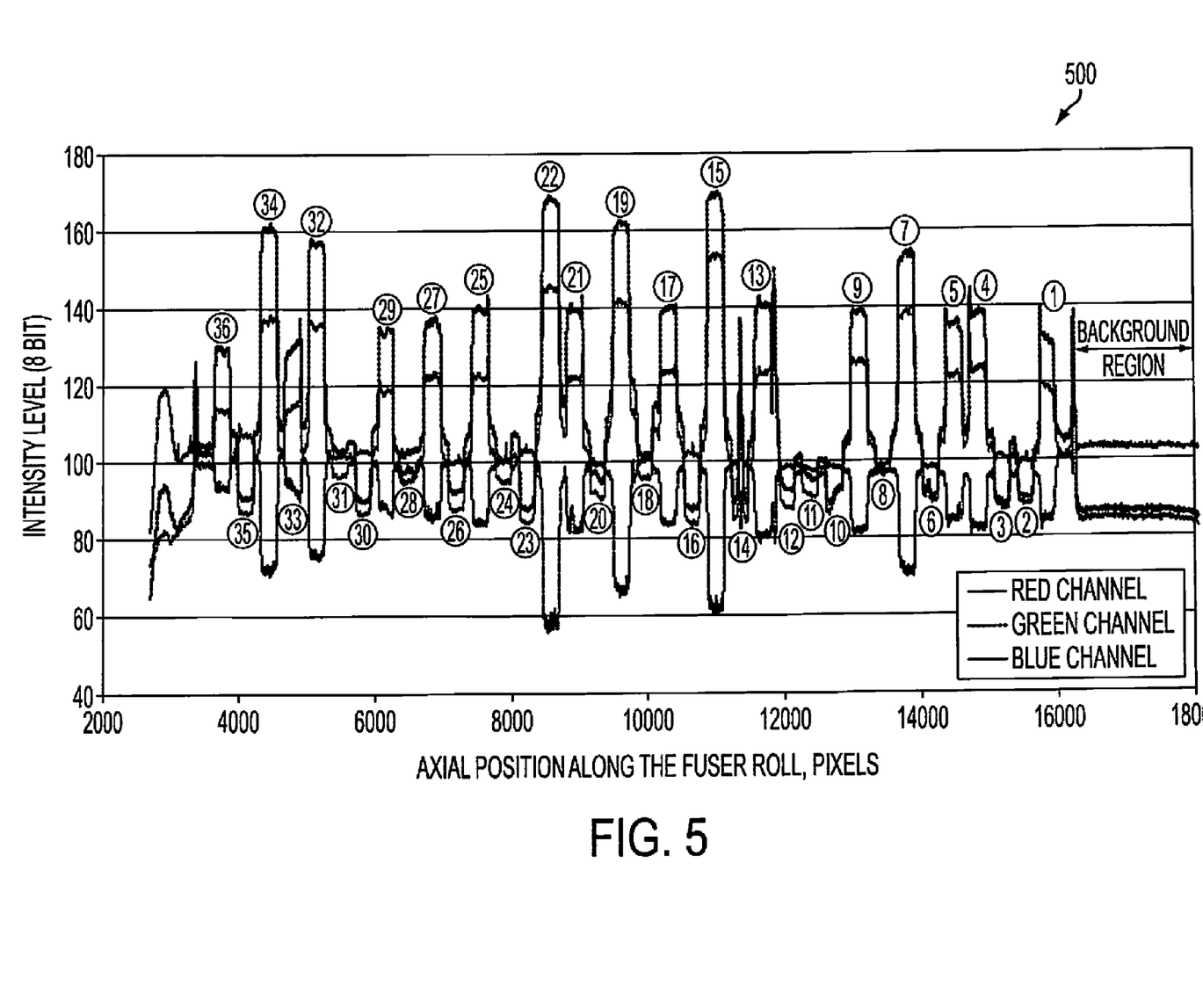
FIG. 5 is a graphic showing RGB intensity data as a function of axial position from a digital picture of the fuser roll of FIG. 4B while illuminated in accordance with the present disclosure.

Referring to the drawings, FIG. 5 shows a chart 500 that graphs RGB intensity data (e.g., data from an RGB sensor that includes photodetector 118 of FIG. 1) as a function of the y-axis of fuser roll 400 of FIGS. 4A and 4B from a digital picture taken with a CCD camera of fuser roll 400 while illuminated. The RGB data shown in FIG. 5 is taken along the axis of fuser roll 400 and may be from multiple digital pictures stitched together. The numbers in FIG. 5 correspond to the stripe numbers shown in FIG. 3, and the large "peaks" in the red and green channels and the large "valleys" in the blue channel exactly correspond to the stripes of test stripe pattern 300 of FIG. 3 that contain magenta. This indicates that a contaminant marker that is on fuser roll 400's surface (of FIGS. 4A and 4B) in the areas associated with the magenta stripes is fluorescing in the yellow part of the spectrum (large peaks in the red and green channels relative to the background) and, at the same time, is absorbing in the blue part of the spectrum (large valleys in the blue channel relative to background). This correspondence may be related to magenta toner because typically the magenta toner in a printing system contains rhodamine dye, a known fluorescent material. In this particular example, the rhodamine dye in the standard magenta toner is playing the role of the fluorescent tag/trace molecules (i.e., the contaminant marker) which indicates certain magenta toners do not need the contaminate marker to be added, to implement a monitoring system, however, in other embodiments a contaminant marker can be added to a possible contaminant source. For example, some possible materials that may be used as contaminant markers are sold under the trademark Lumilux, and include the following article numbers 50104, 50095, 50107, 50105, 50003, 50090, 50085 and 50077 and have the following corresponding article names: Green SN-F25, Green SN-F2, Green SN-F2Y, Green SN-F5, Green N5, Green N-PM, Green N2 and MB Green SN, respectively.

Transforming the RGB signals included in data from an RGB sensor (e.g., data received by analysis module 120 of FIG. 1) to facilitate the estimation of contamination may take multiple forms, use a variety of functions, and the like. For example, consider that system 100 of FIG. 1 includes a multi-channel optical sensor (such as an RGB sensor) and the signal received from the multi-channel optical sensor is used by the analysis module to estimate the contamination of fusing member 102 by using a parameterized model that relates the contamination of the machine component to the data. Other possibilities include using a first function that relates the contamination of the machine component to an area between a channel signal of the signal from the multi-channel optical sensor and a background level of the channel signal of the signal from the multi-channel optical sensor. A second function may be used that relates the contamination of the machine component to a maximum difference between the channel signal of the signal from the multi-channel optical sensor and the background level of the channel signal of the signal from the multi-channel optical sensor A third function may be used that relates the contamination of the machine component to an area under the channel signal of the signal from the multi-channel optical sensor. Yet a fourth function may be used that relates the contamination of the machine component to a peak value of the channel signal of the signal from the multi-channel optical sensor. A fifth function may be used that relates the contamination of the machine component utilizing the background level of the channel signal of the signal from the multi-channel optical sensor. The background levels of the RGB data as shown in FIG. 5 may be determined by the region labeled "background regions". Note that the RGB data is substantially flat in that region. An averaged value may be used within the background region to determine and/or estimate a background level with and/or without data or signal rejection.

Refer simultaneously to FIGS. 4A, 4B and 5, and note that FIG. 5 includes data taken along a line along the y-axis of FIGS. 4A and 4B. Also note that the data shown in FIG. 5 is static in time (e.g., the data has no temporal value). In other embodiments, a spatial map may map the contamination not only along the y-axis of a fuser roll (e.g., fuser roll 400) but also "around" the roll, e.g., along the z-axis wrapped around the rolls. For example, the spatial map may have three axes, one representing the y-axis of FIGS. 4A and 4B, another corresponding to a z-axis that is "wrapped" around the cylinder shape of fuser roll 400, and another axis corresponding to a contaminate, a contaminant marker, a data channel, a plurality of data channels, an equivalent, or some combination thereof. For example, RGB data may be transformed to a corresponding contamination level and that level may form the data for the third axis. Additionally or alternatively, a temporal value may be utilized to estimate contamination, e.g., a contamination rate, a contamination acceleration, a contamination function, a end of life estimate, a predicted contamination level and the like, or some combination thereof.

For example, system 100 of FIG. 1 may identify a particular region that has a corresponding "y" and "x" values along fuser roll 400 that is unacceptably contaminated and may communicate the data to coordinating module 126. Coordinating module 126 may then modify one or more of schedules 1-4 of schedules 136 to avoid printing print jobs that utilize that regions and/or may utilize print jobs that are not likely to have noticeable print defects (e.g., print defects tolerant print jobs).

When estimating contamination by examining a contaminant marker, a background level (e.g., background region of FIG. 5) may be used as a reference in the metric, as mentioned in the previous examples, to improve resolution and/or accuracy. Using a background level provides robustness against DC shifts in the RGB profiles caused by, for instance, variation in the intensity of the illuminant.

Figure 6A:
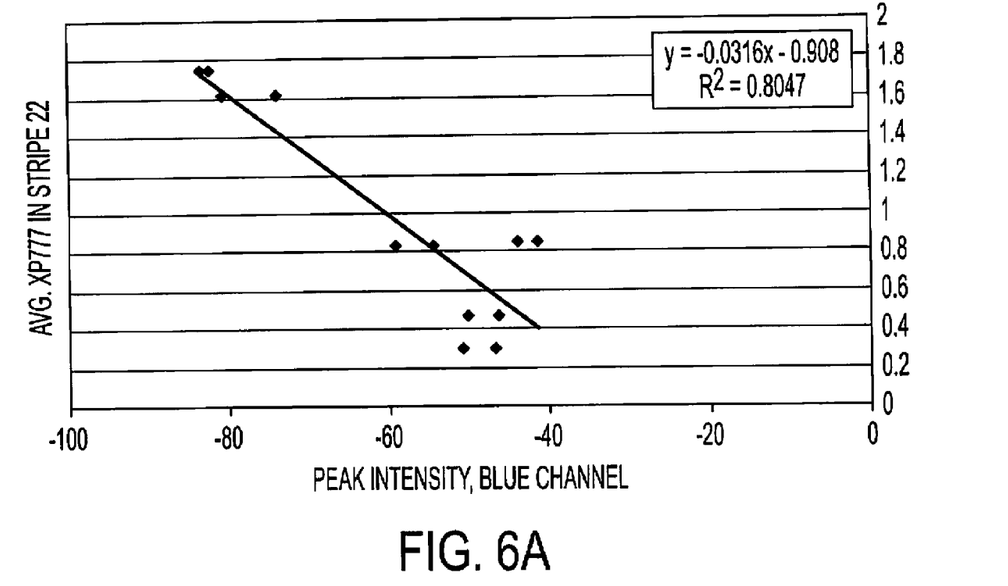
FIG. 6A is a chart that illustrates the correlation between a blue channel peak intensity of a RGB sensor and an average contaminant measured within the region of stripe #22 of the stripe test pattern of FIG. 3 when repeatedly used on a fuser roll in accordance with the present disclosure.
Figure 6B:
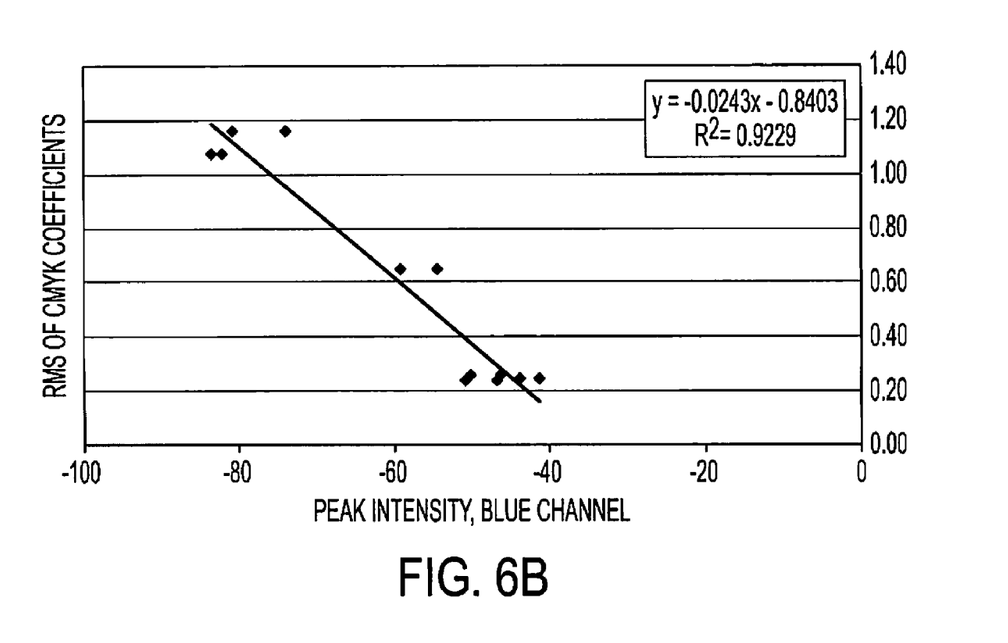
FIG. 6B is a chart that illustrates the correlation between a blue channel peak intensity of a RGB sensor and an overall average contamination measured on the fuser roll when the stripe test pattern of FIG. 3 is repeatedly used on the fuser roll in accordance with the present disclosure.

Referring to the drawings, FIGS. 6A and 6B show two examples of how the peak difference between the blue channel signal and the background level for the blue channel relates to standard metrics of toner resin contamination for each of the 6 rolls under study (12 data points are shown because each roll was measured twice). As shown in FIGS. 6A and 6B this peak differential intensity in the blue channel corresponds to both the level of magenta resin contamination in stripe 22 of FIG. 3 (stripe 22 is where the peak differential intensity occurs) and the overall resin contamination across the entire roll. This exemplary metric may be used by system 100 of FIG. 1 to provide a real-time full-width fuser stress analysis system.

In addition to toner area coverage, the actual stress experienced by a fuser roll (e.g., fuser roll 400 of FIGS. 4A and 4B) also depends on media type, oil rates, environment, material properties, etc., all of which vary within a given machine and from machine-to-machine. System 100 of FIG. 1 can provide a map of the actual stress experienced by fusing member 102 (e.g., a fuser roll) so that the impact of all of these factors is included implicitly. System 100 may be utilized to generate both a spatial map of fusing member 102's surface as well as the time evolution (i.e. one type of time value) of the surface contamination enabling a number of diagnostic, feedback control, and job planning routines and is described below with reference to FIG. 1.

A diagnostics sensing approach could be used to construct and monitor a contamination map of fusing member 102's surface. If the contamination level in a particular region on fusing member 102 has reached a given threshold and an upcoming print job has image content that will contact this region, then the press operator could be alerted via alert module 122 that fusing member 102 needs to be changed before offset or other contamination related defects appear in prints.

Real-time feedback control can be implemented by utilizing fusing set points (temperature, pressure, oil rates, etc) that are adjusted as a function of the contamination via control module 128 in order to mitigate further contamination build-up and/or to compensate for the effects of contamination (e.g. adjusting oil rate can help avoid offset defects). The adjustments may be made automatically and/or with operator intervention. Also, the registration between the unfused image and fusing member 120 could be adjusted to avoid contaminated areas on fusing member 102's surface.

Job planning/sheet scheduling may be implemented by system 100 of FIG. 1 to control a tightly integrated parallel printing system and/or a printing system having a two-stage fusing components. Utilizing this approach could be used to signal the job planner and/or sheet scheduler when one or more contamination thresholds have been reached so that jobs/sheets could be routed to the appropriate fuser and/or print engine, e.g., these may be signals created by coordinating module 126.

Figure 7:
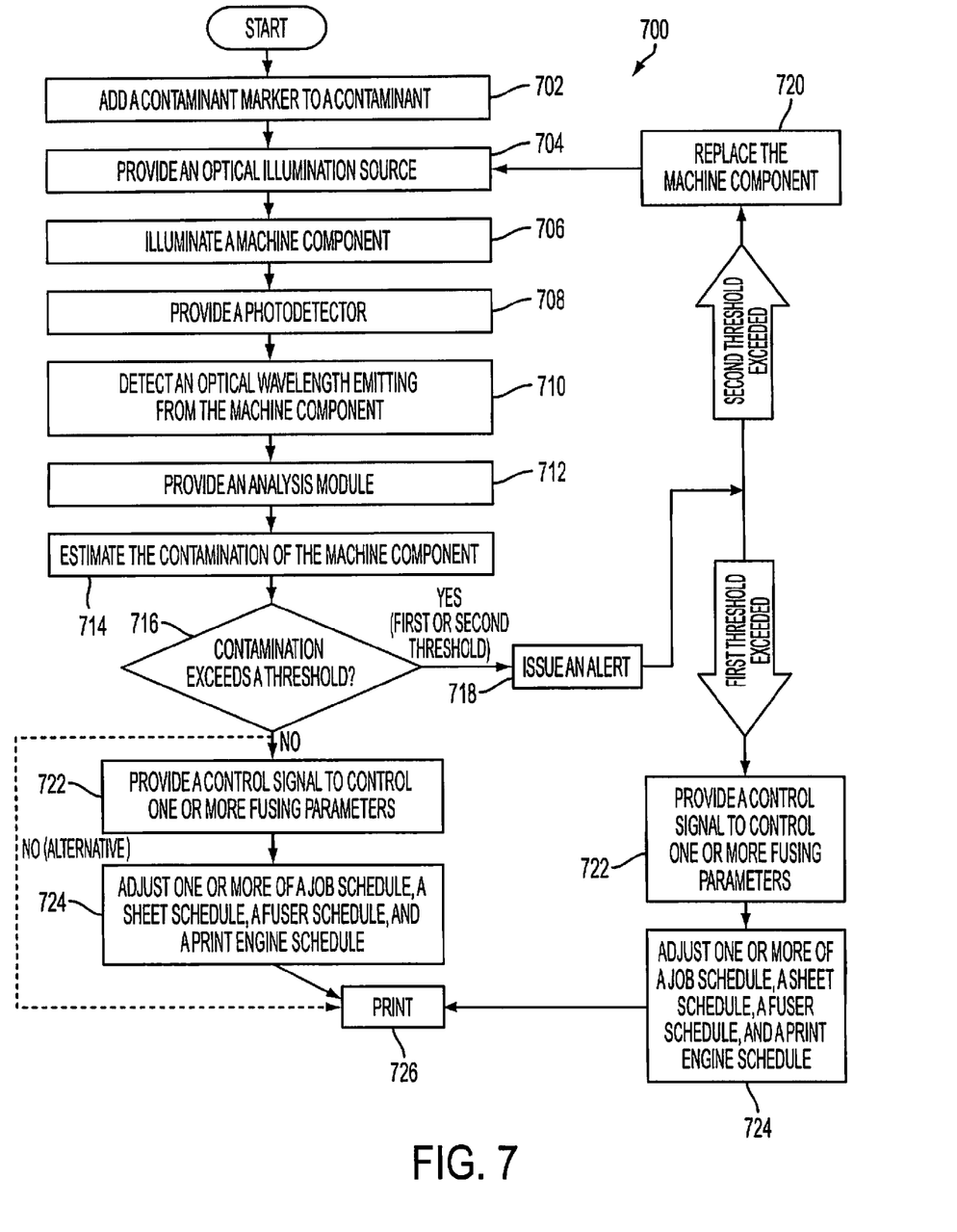
FIG. 7 is a flow chart diagram illustrating a method for optically monitoring contamination of a printer machine component utilizing fluorescent contaminant markers in accordance with the present disclosure.

Referring to the drawings, FIG. 7 is a flow chart diagram illustrating a method 700 for optically monitoring contamination of a machine component utilizing fluorescent contaminant markers. Method 700 includes steps 702 through 730. Step 702 adds a contaminant marker to a contaminant, for example adding rhodamine dye to a magenta toner. Step 702 may be skipped if the magenta toner formulation already contains a contaminant marker, such as the aforementioned rhodamine dye. Step 704 can provide an optical illumination source (e.g., optical illumination source 114 of FIG. 1). Step 706 can illuminate a machine component such as a fusing member. Step 708 can provide a photodetector for use by step 710. Step 710 can detect an optical wavelength emitting from the machine component and may utilize the photodetector of step 708. Step 712 proves an analysis module such as analysis module 120 of FIG. 1. Step 714 can estimate the contamination of the machine component and may utilize the analysis module of step 712.

Step 716 can make a decision based upon the estimated contamination of the machine component as estimated in step 714. If the estimated contamination exceeds a threshold then method 700 may proceed to step 718 to issue an alert. The issued alert may be similar to or the same as the alerts discussed regarding alert module 122 of FIG. 1. If a first threshold is exceeded then machine component 720 may need replacing and method 700 can replace the machine component at step 720. Additionally or alternatively, if another threshold is exceeded then method 700 may utilize step 722 and/or step 724. Step 722 can provide a control signal to control one or more fusing parameters, such as the control signal provided by control module 128 of FIG. 1. Step 724 can adjust one or more of a job schedule, a sheet schedule, a fuser schedule and a print engine schedule, and may be implemented by cording module 126 of FIG. 1. Step 726 can print.

Referring again to step 716 shown in FIG. 7, if a contamination threshold is not exceeded, method 700 may still use steps 728 and 724 as shown before proceeding to step 726 to print. However, an alternative is also shown in which method 700 proceeds directly to step 726 if the estimated contamination does not exceed any thresholds.

It will be appreciated that variations of the above-disclosed and other features and functions, or alternatives thereof, may be desirably combined into many other different systems or applications. Also that various presently unforeseen or unanticipated alternatives, modifications, variations or improvements therein may be subsequently made by those skilled in the art which are also intended to be encompassed by the following claims.

What is claimed is:

1. A system for optically monitoring contamination of machinery, comprising:
    an optical illumination source configured to emit at least one illuminating frequency, wherein the at least one illuminating frequency is configured to cause a contaminant marker to fluoresce at least one fluorescing frequency, wherein the optical illumination source is also configured to at least partially illuminate a machine component, wherein the machine component contains the contaminant marker when at least partially contaminated;
    a photodetector responsive to the at least one fluorescing frequency, wherein the photodetector is configured to detect the at least one fluorescing frequency emitting from the contaminated machine component; and
    an analysis module in operative communication with the photodetector and configured to receive a signal therefrom, wherein the analysis module is configured to estimate contamination of the machine component as a function of the signal from the photodetector.

2. The system according to claim 1, wherein the machine component is a printer machine component.

3. The system according to claim 2, wherein the printer machine component is a fusing member, wherein the fusing member is one of a fuser roll and a fuser belt.

4. The system according to claim 1, wherein the system further comprises one of a full-width array sensor including the photodetector and a camera including the photodetector.

5. The system according to claim 1, wherein the contaminant is at least one of cyan toner, magenta toner, yellow toner and black toner.

6. The system according to claim 1, wherein the contaminant marker is rhodamine dye included in magenta toner.

7. The system according to claim 1, the system further comprising:
    an alert module in operative communication with the analysis module, wherein the alert module is configured to issue an alert when the estimated contamination of the machine component exceeds a threshold.

8. The system according to claim 1, wherein the optical illumination source is a black light.

9. The system according to claim 1, wherein the optical illumination source is a near-ultraviolet illumination source.

10. The system according to claim 1, the system further comprising:
    an indicator module in operative communication with the analysis module, wherein the indicator module is configured to provide at least one indication corresponding to the estimated contamination of the machine component.

11. The system according to claim 1, the system further comprising:
    a control module in operative communication with the analysis module, wherein the control module provides a control signal, wherein the control signal is a function of the estimated contamination of the machine component.

12. The system according to claim 11, wherein the machine component is a fusing member and the control signal is configured to control at least one fusing parameter, wherein the at least one fusing parameter includes at least one of a fusing temperature, an oil rate, a fusing pressure, a registration and a registration offset.

13. The system according to claim 11, wherein the system further comprises a coordinating module and the machine component is a printer machine component, wherein the coordinating module adjusts at least one of a job schedule, a sheet schedule, a fuser schedule, and a print engine schedule to account for the estimated contamination.

14. The system according to claim 1, wherein the estimated contamination of the machine component is a function of at least one of a spatial value and a temporal value.

15. The system according to claim 1, wherein the analysis module utilizes the estimated contamination of the machine component to generate a contamination spatial map.

16. The system according to claim 1, the system further comprising:
    a sensor controller in operative communication with the analysis module and the photodetector, wherein the sensor controller is configured to calibrate the analysis module by estimating at least one background level.

17. The system according to claim 1, the system comprising a multi-channel optical sensor including the photodetector, wherein the analysis module receives the signal from the multi-channel optical sensor and is in operative communication with the multi-channel optical sensor, wherein the analysis module estimates the contamination of the machine component using at least one of:
    a parameterized model that relates the contamination of the machine component to the signal from the multi-channel optical sensor;
    a first function that relates the contamination of the machine component to an area between a channel signal of the signal from the multi-channel optical sensor and a background level of the channel signal of the signal from the multi-channel optical sensor;
    a second function that relates the contamination of the machine component to a maximum difference between the channel signal of the signal from the multi-channel optical sensor and the background level of the channel signal of the signal from the multi-channel optical sensor;

a third function that relates the contamination of the machine component to an area under the channel signal of the signal from the multi-channel optical sensor;

a fourth function that relates the contamination of the machine component to a peak value of the channel signal of the signal from the multi-channel optical sensor; and a fifth function that relates the contamination of the machine component utilizing the background level of the channel signal of the signal from the multi-channel optical sensor.

18. A method for optically monitoring contamination of machinery, comprising:

providing an optical illumination source configured to emit at least one illuminating frequency, wherein the at least one illuminating frequency is configured to cause a contaminant marker to fluoresce at least one fluorescing frequency, wherein the optical illumination source is also configured to at least partially illuminate a machine component, wherein the machine component contains the contaminant marker when at least partially contaminated;

providing a photodetector responsive to the at least one fluorescing frequency, wherein the photodetector is configured to detect the at least one fluorescing frequency emitting from the contaminated machine component; and providing an analysis module in operative communication with the photodetector and configured to receive a signal therefrom, wherein the analysis module is configured to estimate contamination of the machine component as a function of the signal from the photodetector

19. The method according to claim 18, wherein the machine component is a printer machine component.

20. The method according to claim 18, wherein the printer machine component is a fusing member, wherein the fusing member is one of a fuser roll and a fuser belt.

21. The method according to claim 18, wherein the method further comprises the step of:

adding the contaminant marker to a contaminant.

22. The method according to claim 18, wherein the method further comprises the step of:

replacing the machine component when the estimated contamination of the machine component exceeds a threshold.

23. The method according to claim 18, wherein the method further comprises the step of:

issuing an alert when the estimated contamination of the machine component exceeds a threshold.

24. The method according to claim 18, wherein the machine component is a fusing member, wherein the method further comprises the step of:

providing a control signal configured to control at least one fusing parameter, wherein the at least one fusing parameter includes at least one of a fusing temperature, an oil rate, a fusing pressure, a registration and a registration offset.

25. The system according to claim 18, wherein the machine component is a printer machine component, wherein the method further comprises the step of:

adjusting at least one of a job schedule, a sheet schedule, a fuser schedule and a print engine schedule to account for the estimated contamination.

* * * * *